United States Patent [19]
Freeman

[11] Patent Number: 4,718,905
[45] Date of Patent: Jan. 12, 1988

[54] HAPTIC ELEMENT USING ION BEAM IMPLANTATION FOR AN INTRAOCULAR LENS

[76] Inventor: Jerre M. Freeman, 1509 Peabody, Memphis, Tenn. 38104

[21] Appl. No.: 895,944

[22] Filed: Aug. 13, 1986

[51] Int. Cl.⁴ .......................... A61F 2/16; A01N 1/02
[52] U.S. Cl. ............................................ 623/6; 427/2
[58] Field of Search ............................. 623/6; 427/2

[56] References Cited

U.S. PATENT DOCUMENTS

| | | | |
|---|---|---|---|
| 4,174,543 | 11/1979 | Kelman | 623/6 |
| 4,298,995 | 11/1981 | Poler | 623/6 |
| 4,363,143 | 12/1982 | Callahan | 623/6 |
| 4,404,694 | 9/1983 | Kelman | 623/6 |
| 4,418,431 | 12/1983 | Feaster | 623/6 |

OTHER PUBLICATIONS

Dubroff Model 044B Anterior Chamber Lens (advertisement) Intermedics Intraocular, 2 pages, Jan. 1984.
Apple et al, "Biocompatibility of Implant Materials: A Review and Scanning Electron Microscopic Study", Am. Intra-Ocular Implant Soc. J., vol. 10, pp. 53–66 (1984).
Sionshansi, P., "Ion Beam Modification of Materials for Industry", Thin Solid Films, vol. 118, pp. 61–71 (1984).
Sionshansi, et al, "Wear Improvement of Surgical Titanium Alloys by Ion Implantation", J. Vac. Sci. Technol., A 3(b), pp. 2670–2674 (Nov./Dec. 1985).
Surface Modification by Ion Beams", by Spire Corporation, 4 pages (brochure).

Primary Examiner—Ronald L. Frinks
Attorney, Agent, or Firm—Burns, Doane, Swecker & Mathis

[57] ABSTRACT

An implantable intraocular lens for use within a human eye is provided with enhanced carrier or haptic loops for locating, supporting and maintaining the lens device in a desired position within the ocular chamber of an eye. Enhanced haptic longevity and biocompatibility is provided by a surface ion coating the polypropylene haptic on at least the surfaces making tissue contact. The biocompatible protective ion coating is applied by ion beam implantation. The biocompatible protective ion coating is preferably nitrogen, carbon, silicon or aluminum.

21 Claims, 8 Drawing Figures

HAPTIC ELEMENT USING ION BEAM IMPLANTATION FOR AN INTRAOCULAR LENS

This application relates in part to my application U.S. Ser. No. 893,909 filed concurrently herewith, entitled "Improved Haptic Element for An Intraocular Lens" which is directed to coating a haptic with a polymer, metal or metallic alloy, carbonaceous material or glass.

TECHNICAL FIELD

The present invention relates to an improved intraocular lens device for implantation within a human eye following removal of a natural crystalline lens. More particularly, this invention relates to an enhanced lens carrying loop or haptic to provide improved loop longevity and biocompatibility without detracting from the advantageous features and structure of the haptic.

DESCRIPTION OF THE BACKGROUND ART

The concept of implanting an intraocular lens as a replacement for an opaque crystalline lens of a human eye was suggested as early as 1766 by Cassanova in his memoirs. It has been only within the last thirty-five years or so, however, that theory and desire, have become a practical reality. In this connection, the first lens implantation is believed to have been carried out in 1949 by Dr. Harold Ridley at the Thomas Hospital in London. A lens was inserted into the posterior chamber of a woman about sixty years of age following cataract extraction. Dr. Ridley's early efforts achieved a degree of success and ophthalmic surgeons began implanting lenses composed of polymethylmethacrylate (PMMA) within the posterior chamber of the human eye following extracapsular removal of a cataract to restore binocular vision to patients.

Notwithstanding initial successes, drawbacks were also encountered. Early posterior chamber lens implantation reported incidences of dislocation, iris atrophy from pressure of the rim of a badly centered lens, and secondary glaucoma.

In addition to posterior chamber implantation, the attention of early surgeons also focused on the anterior chamber as a location for placement of an intraocular lens. Relatively rigid lenses were designed by Dr. Strampelli to be mounted within the anterior chamber and supported by the anterior chamber angle. A major disadvantage of rigid anterior chamber lenses was the danger it posed to the corneal endothelium and other delicate structures of the eye which are very sensitive to pressure or contact. The endothelium is a corneal cellular layer which may die upon touching and usually does not regenerate. More particularly, a lens that was too short would tend to move around inside the eye, twisting and turning on its axis, creating problems that were often complicated by endothelial corneal dystrophy. In contrast, a lens that was too long tended to distort the eye globe and damage angle structures.

Many of the difficulties encountered with rigid structures were alleviated, to a degree, by the development of flexible supports or loops by Dr. Dannheim. Even flexible loops, however, are subject to size limitations. Moreover, excessive flexibility or breakage of the supporting loops presented a danger to the iris and corneal endothelium. Additionally, flexible loop haptics were often designed with only three or four points of contact. Accordingly, eye tenderness was frequently encountered. In order to obviate eye tenderness some designs extended the length of contact of the flexible loop with the anterior chamber until a bearing ring was functionally created. When the loops were extended substantially around the periphery of the anterior chamber angle, however, interference was often encountered with the proper functioning of the sinus venosus sclerae (Schlemm's canal).

Although significant achievements were realized in the 1950s and 1960s, as late as 1968 there were still only about three choices for ophthalmologists desiring to implant intraocular lenses: a Choyce lens, an iris-plane lens and a four-loop Binkhorst lens. Within the last decade, however, lens design has expanded considerably and in 1982 approximately 175 intraocular lens designs were available from sixteen companies.

Currently in most intraocular lens designs, a PMMA lens is supported and held in place by a plurality of support strands or haptics. Each of the haptics is attached or secured to the peripheral lens body edge and each is flexible, that is to say each strand must be yielding under pressure, but must also have a memory retaining feature whereby the strand will return to its normal extended position or will automatically tend to do so once contact pressure has been released. Thus, the haptics have a spring-like quality and are normally composed of a biologically inert plastic material.

The haptics are attached to the lens body by any convenient or desirable means. One means is to have a hole provided in the lens periphery by boring, drilling or molding and to insert one end of the haptic into the hole and secure the haptic by an adhesive, interference or other mechanical means.

An arched distal end of the strand or loop provides a rounded haptic surface to contact the eye tissue once the lens is implanted. The longer and more gradual the arch, the less likely there will be any injury or trauma to the ciliary body tissue against which the arched strand abuts.

In the 1950s and 1960s nylon in various polymeric forms gained widespread popularity both as a loop material and as a fixation suture due to its strength, handling characteristics and believed durability. Despite initial success, cases of breakage and degradation of nylon were reported. Surface roughness and cracking in nylon sutures have been shown by scanning electron microscope. The hydrophilic tendencies of nylon led at least some investigators to believe that hydraulic degradation was at fault. In any event, nylon was discontinued as a haptic material by most manufacturers in 1979.

In the 1978–79 time frame, the advantages of polypropylene were recognized including low specific gravity and thus buoyancy support for a lens, nonabsorbability, relative inertness and stability, elasticity, minimal tissue reactivity, strength in the post-operative period, resistance to bacterial contamination and good tolerance by the patient. A proprietary FDA approved polypropylene is Ethicon brand "Prolene" supplied by Ethicon Pharmaceutical Company. Such material has superior qualities over other strand or loop materials such as gut, silk and nylon. The former materials, although flexible, do not achieve the desired buoyancy or spring-like memory retention qualities. The spring-like qualities of the strands which are continually urged to their greatest extension and are slightly compressed on their fully extended position maintain the lens body correctly centered in the ciliary space and posterior chamber. Thus, the springy haptics are biased and urged against the ciliary body to achieve desired centering and fixation of the intraocular lens.

Notwithstanding the advantages detailed above, in at least some quarters polypropylene haptics began to be investigated by clinical evaluation and laboratory research relating to the biocompatibility of the polypropylene when used in the intraocular lens loops or footplates. Scanning electron microscope findings of the morphology of haptics from removed intraocular lenses indicate possible alterations demonstrably connected to in-vivo changes. These alterations may be interpreted as resulting from a broad spectrum of situations, ranging from harmless manufacturing defects, to stress cracking, to possible progression toward actual loop degradation. In particular, an article titled "Biocompatibility of Implant Study" by Dr. David J. Apple et al. printed in *American Intra-Ocular Implant Society Journal*, Volume 10, Number 1, Winter 1984, addressed many of those problems. Widespread potential complications have been considered in view of observed in-vivo changes in the haptic material and the present invention comprehends prior concern over possible immune and inflammatory reactions, erosions into tissue, hemorrhage, or possible lens dislocation.

With the refinement of the art of lens design and manufacturing and with increased experience in ophthalmic surgery, surgeons' lens implantation is now one of the safest procedures in modern surgery. It has been reported that 496,000 or nearly one half million intraocular lenses were implanted in the United States alone between Feb. 1982 and Feb. 1983. It is envisioned by many that this figure will soon top one million per year. With the increased success in recent surgical developments, intraocular lenses now are being implanted in young adults, in children and in patients with borderline or low corneal endothelial cell counts, in monocular patients and in patients with various preexisting ocular and systemic diseases.

Preliminary findings indicate that changes in polypropylene haptic material may be time related and more severe changes are observed in highly metabolic tissue such as the ciliary sulcus. It is believed that induced irregularities in the loop surface cause exaggerated irritation due to mechanical rubbing against adjacent tissues leading to complications such as breakdown of the blood-aqueous barrier, release of prostaglandins or oxidating agents, or inflammation.

Haptic materials discussed above have included nylon and polypropylene both of which have been used successfully over the years in intraocular lenses. Other support materials include metal loops of various types but such structures have been found unacceptable because of several complications related to weight and fixation.

Some intraocular lenses employ haptic footplates in place of a loop or strand and these plates extend from the lens body, which is usually made of PMMA, and terminate in rounded or blunt shapes for seating in an eye chamber. Here the materials for the footplates have also included PMMA and most recently soft materials such as soft hydrogels or hydrophilic type such as 2-hydroxyethyl methacrylate, generally referred to as PHEMA.

As with the metal loops, the haptic footplates add extra material weight to the lens structure when compared to the loops or strand haptics.

Another intraocular lens available today is a PMMA lens body with haptics comprised of PMMA loop material. While these PMMA loops provide an excellent ocular prosthesis, the PMMA material is stiffer than polypropylene and can be quite difficult to remove when necessary. Additionally, some patients believe they can feel the pressure of PMMA loop material in an eye. This is especially prominent when a patient has a polypropylene loop intraocular lens in one eye, showing no discomfort, and reports a kind of "pressure feeling" in the other eye where an all PMMA loop intraocular lens resides.

Not only are different materials known for use in an intraocular lens but it has been known to use a different material for the haptics than for the lens itself. Specifically, U.S. Pat. No. 3,996,627 teaches an intraocularly implantable lens of glass wherein the haptics are constructed entirely of strands of plastic material, e.g., extruded Teflon, or of metal, e.g., platinum, titanium or tantalum wire. Thus, the lens and the haptics are composed of two different materials.

It is also known to use a coating of silicone rubber on a metal or plastic member. German Patent No. 25 56 665 teaches an intraocular lens where the haptic edge has an elliptic contour with a bulge at a secondary epice and wherein the optical portion is made entirely of silicone rubber. Methylsiloxanes or methylphenysiloxanes are the preferred materials for making the silicone rubber material, but it is also suggested to use siloxanes in which the remaining valences of silicone are saturated with propyl and phenyl groups. It is suggested that the optical portion and the haptic edge, surrounding the optical part, can be manufactured from one single piece of silicone rubber, while the haptics are made of metal or plastic and can be coated with a layer of silicone rubber.

U.S. Pat. No. 4,172,297 also discloses a lens of transparent material such as silicone rubber having a central lens body having front and rear ends, and two discs adapted to overlap the edge of the iris which surrounds the pupil with an annular space being formed between the discs and the space widening towards its outer edge for receiving the pupil edge of the iris.

In view of the relative satisfaction found with haptic materials currently in use today, amazingly little attention has been extended to the concept of coating the haptics in an attempt to achieve haptics of extended wearability.

It has recently been discovered that it is possible to alter only the surface of certain materials such as metals, ceramics, silicon and plastics using a process known as ion beam implantation (IBI). The process involves firing electrically charged atoms (ions) at a material to achieve a variety of results. These results include prolonged material wear, superior conductive (or insulating) properties, oxidation- and corrosion-resistance, reduction of surface friction and alterations in magnetism and other intrinsic properties.

In addition, because of their physical and/or chemical structure, many substances cannot be combined even though the properties of each may be extremely desirable when paired. An example would be the conductivity of metal with the corrosion-resistance of ceramic. Ion implantation allows such mixing to occur at the surface level of the material. Through a technique known as "sputtering", invisible beams of one or more materials are "sprayed" onto another material. The ions impregnate the surface, creating a new material with the attractive characteristics of all its component substances.

In the last few years, the use of ion beams to charge the surface properties of materials has gained increasing attention. Atoms of many ionizable elements have been excited to high speeds and shot into the surface of a variety of solid materials. Ionization is the process by which atoms or groups of atoms assume a net electrical charge by losing or gaining electrons. This process is known as on-beam processing or ion-beam implantation and its major use at the present time is in the semi-conductor industry, where silicon is doped to alter its electrical properties. The most recent developments are in the treatment of metal, ceramic, glass or polymeric surfaces to upgrade hardness, optical properties, corrosion resistance, electrical conductivity, and other characteristics. Such elements as nitrogen, argon, boron, platinum, rhodium, phosphorus, chromium, and polybdenum have been implanted in steel (and many of its alloys), titanium, and copper, as well as in glasses and ceramics.

Nitrogen implantation is the process most heavily researched and easiest to perform and it was one of the first commercial applications for ion-beam implantation. Generally, the nitrogen ions emerge from an ionization chamber as part of a 50-50 mixture of ions and charged molecules. The nitrogen ions make the material or substrate more durable, reduce surface flaws and minimize other defects, and prevent spalling (peeling away of the surface layer) and other types degradation. One example is nitrogen treatment of surgical bone implants. In many such prostheses, this treatment reduces wear rates by a faction of 400 or more. Implants have also been treated with carbon with good results. The surface wear has been reduced to negligible levels and greatly extends the useful life of the implant.

The greatest research effort has been in the area of metals as previously indicated. At the present time little emphasis has been placed on the treatment of polymers with ion beam implantation. For instance, it has been determined that the electrical conductivity of polyacetylene may be enhanced by bombarding it with ionized conducting metals. In addition, injection molds, nozzles and bushes used in the plastics industry have been treated with nitrogen. Abrasive fillers in plastic material present a serious erosive problem in plastic injection molding operations. Thus, nitrogen implantation has been used for protecting the expensive mold surfaces. However, the biomedical applications of polymers coated by ion implantation have not received any attention.

The subject invention goes beyond anything offered by the prior art especially the prior art covering intraocular lenses and is directed toward an improved haptic loop and makes available to the surgeon and wearer an intraocular lens having superior material characteristics thereby extending the usable life of the haptic surface and ensuring the patient of many years of satisfactory service from an intraocular lens.

The problems suggested in the preceding are not intended to be exhaustive, but rather are among many which may reduce the effectiveness and user satisfaction of prior haptic carrier devices. Other noteworthy problems may also exist; however, those presented above should be sufficient to demonstrate that haptic loop material appearing in the past will admit to worthwhile improvement.

The subject invention is directed toward an improved haptic providing for enhanced haptic longevity and biocompatibility without detracting from the advantageous features of prior devices. More particularly, the present invention is directed to the use of a coating process for haptics which would protect the haptics and make them resistant to corrosion or oxidation thereby extending their useful life.

OBJECTS OF THE INVENTION

Thus, it is a general object of the invention to provide a novel, intraocular lens having haptics which will obviate or minimize difficulties of the type previously described.

It is a specific object of the invention to provide a novel, intraocular lens having haptics which will not expose a wearer to the potential detrimental effects of bioerodable fluids and tissue present in an eye cavity.

It is a specific object of the invention to provide a novel, intraocular lens which is coated and thus provides enhanced haptic longevity or in-vivo service life and which employs known and medically accepted materials to maintain the specific gravity and flexibility of conventional haptic carrier elements.

It is another object of the invention to provide a novel intraocular lens having haptics and which employs more efficacious haptic material having properties making it less susceptible to "checking" or "alligatoring" which have been observed by scanning electron microscopy with polypropylene haptic strands.

It is a further object of the invention to provide a novel, intraocular lens having haptics which has increased patient acceptance by minimizing intraocular lens replacement due to failure of haptic members.

Still another object of the invention is to provide a novel, intraocular lens having haptics which will provide an ophthalmic surgeon with an intraocular lens providing enhanced patient comfort.

SUMMARY OF THE INVENTION

It has now been determined in accordance with the present invention that an implantable intraocular lens has been developed with enhanced carrier or haptic loops for locating, supporting and maintaining the intraocular lens in a desired position within the ocular chamber of an eye. Enhanced haptic longevity and biocompatibility is provided by applying an ion by ion beam implantation on the haptic or on at least the apical surface of the haptic which makes contact with living tissue upon placement within the eye. The ion coating is a biocompatible protective covering which partially or completely coats the haptic to enhance the longevity or in-vivo service life of the haptic and shields the haptic from the detrimental and bioerodable effect of body fluids, ultraviolet light and tissue contact. A particularly preferred embodiment for the implantable intraocular lens of the present invention has a polymethylmethacrylate body and polypropylene haptics with an ion coating of nitrogen, carbon, silica or alumina.

BRIEF DESCRIPTION OF THE DRAWINGS

Other objects and advantages of the present invention will become apparent from the following detailed description of the preferred embodiment thereof taken in conjunction with the accompanying drawings wherein.

DETAILED DESCRIPTION OF THE PREFERRED EMBODIMENTS

Figure 1:
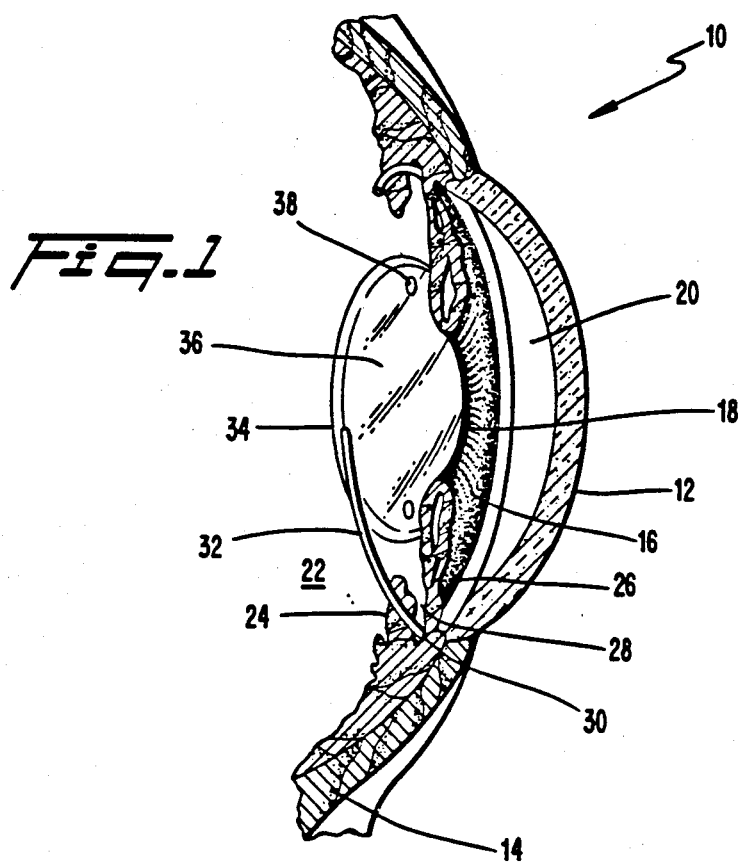
FIG. 1 is an axonometric partial cross-sectional view of a human eye disclosing the context of the instant invention.

Before presenting a detailed description of the subject intraocular lens device, it may be worthwhile to briefly outline the context of the instant invention. In this connection, FIG. 1 depicts the use of a surgically implantable intraocular lens prosthesis which may advantageously employ the biocompatible protective coating of the subject invention.

Although the eye 10, like any other biological structure, may vary in size, 24 millimeters may be taken as an average of all three main diameters (i.e., the anterior-posterior, or sagittal, the transverse, and the vertical). The posterior half of the eyeball closely approaches a spherical shape, while a forward or anterior portion is provided with a roughly spherical segment of sharper curvature which is transparent and called the cornea 12. An opaque posterior portion is known as the sclera 14.

The cornea 12 is constructed in such a way as to serve as a refracting medium in addition to forming the anterior wall of the eyeball. The cornea is a strongly convergent lens and possesses approximately two-and-one-half times the focusing power of an internal crystalline lens. An iris 16 of variable aperture, known as the pupillary opening or pupil 18, is positioned behind the cornea 12 and divides the eye into a anterior chamber 20 in front of the iris and a posterior chamber 22 behind the iris. The natural crystalline lens is connected by zonular fibers to a peripheral muscle about the lens known as the ciliary muscle 24.

When the natural crystalline lens, which in a normal healthy condition is transparent, becomes cloudy and opaque to the transmission of light, a cataract condition exists and in order to correct this impairment, the cataract lens must be removed. The patient is then fitted with specially designed eyeglasses or with an intraocular lens to restore the patient's binocular vision.

A peripheral limit of anterior chamber angle 26 exists between the base of the iris and a scleral spur and operably serves as a support location for an intraocular lens device implanted within the anterior chamber 20 of the eye. A peripheral zone 28 also exists within the posterior chamber between the ciliary muscle 24 and the base of the iris 16, and is known as the ciliary sulcus 30. This peripheral rim operably serves as a mounting location for an intraocular lens within the posterior chamber 22.

As disclosed in FIG. 1, it will be seen that the natural crystalline lens of the eye 10 has been removed during cataract surgery and an intraocular lens device has been positioned in the posterior chamber and is supported by haptics 32 bearing upon the ciliary sulcus 30.

Another position which may serve as a mounting location for an intraocular lens is formed during extracapsular extraction cataract surgery by removal of an outer anterior layer of a lens capsule which enhouses the crystalline lens. Removal of the internal crystalline lens operably leaves a capsular bag. This bag is relatively inert, having no nerve endings and no blood vessels.

The haptic members 32 exhibit a generally smoothly contoured surface in the form of a lazy "J" having the stem connected to the lens periphery 34. The haptic member 32 is preferably formed from a solid, rod-like, polymer member of circular cross-section and is designed to be relatively thin and flexible while providing adequate supporting strength for the lens 36. Materials which have been found to be most suitable for this purpose include polypropylene and polymethylmethacrylate. Other materials, however, may be utilized as desired. Typical haptic materials include, but are not limited to, polypropylene (PP), polymethylmethacrylate (PMMA), polycarbonate, polyacrylate, 2-hydroxymethyl-methacrylate, nylon, extruded Teflon, stainless steel, platinum, titanium, tantalum, and the like. The preferred haptic material is polypropylene. The arched end of the haptic J-loop provides a rounded surface to contact the eye tissue and the long, gradual arch of the haptic strand minimizes injury or trauma to the ciliary body tissue against which the arched strand abuts. The spring-like qualities of the loops maintain the lens body in correct position within the ocular chamber.

The haptic members intended for use in the practice of the present invention may have a variety of shapes. The most common haptic members include the J-loops, S-loops and C-loops. In particular, note representative U.S. Pat. Nos. 4,174,543; 4,298,995; 4,363,143; 4,404,694; and 4,418,431 which are hereby incorporated by reference as though set forth at length.

In order to facilitate insertion and positioning of the intraocular lens device within either the anterior or posterior chamber of an eye, a pair of apertures 38 are typically fashioned through the rim of the lens 36 as desired. First and second haptic members are symmetrically mounted with respect to the lens 36 and the mountings 34 are diametrically opposed.

As the residence time of the haptic material implant increases, surface deteriorations may require replacement of the intraocular lens device to obviate ocular irritation.

A call to investigate improvements in polypropylene haptic materials appeared in an article titled "Biocompatibility of Implant Materials: A Review and Scanning Electron Microscope Study" by Dr. David J. Apple et al. printed in *American Intra-Ocular Implant Society Journal*, Volume 10, Number 1, Winter 984. The material appearing in this article is hereby incorporated by reference as though set forth at length.

Figure 2:
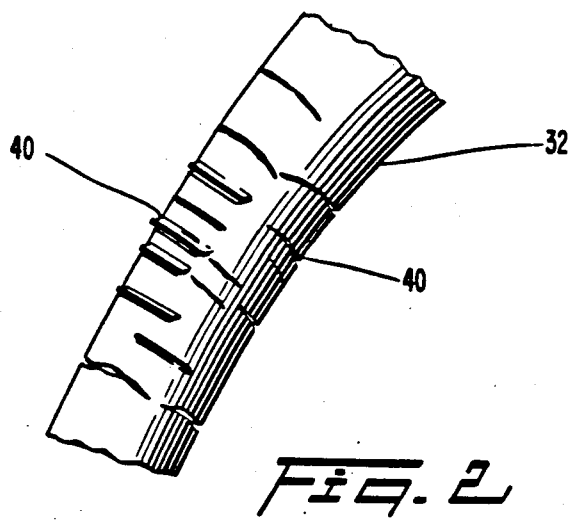
FIG. 2 is an axonometric view depicting a section of a prior art haptic like that shown in FIG. 1, which has been enlarged by an electron microscope approximately 100 times its actual size.

With reference to FIG. 2, a view is presented of a prior art polypropylene haptic loop 32, magnified approximately 100 times, showing alterations in a loop section that had been embedded in a wearer's ciliary sulcus for forty-five months before enucleation of the eye. Surface alterations have been detected on polypropylene intraocular lens loops by scanning electron microscopy. Various degrees of surface rupture can be detected ranging from numerous, fine, nonelevated, delicate, transverse fissures located only on the apical or outer segments of loops to larger segments of the polypropylene curling up from the loop surface to expose secondary cracking below the exfoliated superficial layer. Moreover, some degradation can be observed encompassing virtually the entire circumference of the loop.

Various fissures or cracks 40, perpendicular to the long axis of the loop were observed to correspond to the portion of the loop that had eroded most deeply into the ciliary sulcus and was embedded into the tissue near the iris circle. The ciliary sulcus is a highly metabolic body which is believed to accelerate the degradation of polypropylene haptic material.

While the nature of these cracks or "alligatoring" is not entirely understood, it is clear that improvements obviating such observed degradation of loop material would be desirable.

Turning now to FIGS. 3-7, there will be seen illustrative embodiments of the subject enhanced haptic for an intraocular lens.

Figure 3:
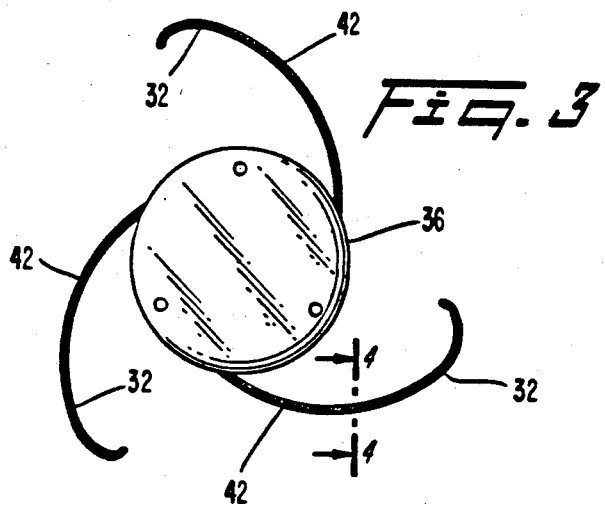
FIG. 3 is a plan view of an intraocular lens and haptic which advantageously employ the subject invention and shows a coating on the haptic strands.
Figure 4:
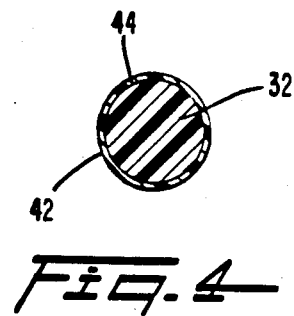
FIG. 4 is a cross-sectional view taken along section line 4—4 in FIG. 3.

The embodiment presented in FIGS. 3 and 4 comprises one of a plurality of presently known lens designs. The lens body 36 is composed of PMMA and the haptics 32 are fashioned from polypropylene strand material. Each haptic strand 32 is coated with a biocompatible protective covering material 42 extending around the full circumference 44 of the haptic strand. Such an arrangement provides maximum encasement of the haptic to protect it from the bioerodable effects of ocular tissue.

In determining the preferred qualities of a material suitable for coating the haptics the primary concern is that the coating material must be compatible with the environment of the eye. The terms generally describing this property include biocompatible and inert. Since the purpose of the coating is to protect and thereby extend the life of the heptic material tself, the coating should be relatively non-corrosive. The coating material should have some amount of flexibility, stability and smoothness. The smoothness is particularly important in order to obtain the desired surface texture. The coating is also preferably non-magnetic to avoid a battery-like activity within the eye. Finally, it would be most desirable if the coating material lent itself to relative ease of workmanship.

Based on the foregoing desirable properties, coating of the present invention is the result of ion beam implantation.

Ion beam implantation has many advantages over conventional surface treatments such as coatings, laminates and diffusion techniques. These advantages include no dimensional changes, no coating to peel off or delaminate, a low temperature process, and highly controllable and easily reproducible.

Suitable elements used to produce the ions for the ion coating on the haptics of the present invention include, but are not limited to, nitrogen, carbon, silicon, aluminum, tin, titanium, boron, nickel, chromium, zirconium, gold, germanium, xenon, platinum, phosphorus, yttrium, hafnium, rhodium, molybdenum, tantalum and combinations thereof. The preferred ions useful in the practice of the present invention are nitrogen, carbon, silicon and aluminum. The most preferred ion is nitrogen.

Ion implantation is conducted in a vacuum to prevent chemical contamination and ion scattering. The typical ion-beam generator, call a Freeman source, is a metal cylinder containing a filament that throws off electrons when electrically charged. The element to be implanted (or a compound containing the element) is first vaporized, then ionized as it collides with the electrons. The resulting ions can be either positive or negative, depending on the element.

If metal ions are to be implanted, the metal must first be converted into a chemical that vaporizes readily. Titanium, for example, can be converted to titanium chloride. In this case, ionization produces a vapor consisting of both titanium and chlorine ions; the latter can be extracted by magnetic fields.

A combination of magnets and electric coils can then be used to direct, purify, and concentrate the mass of ions into a tightly focused beam. The energized beam smashes into the target material (called the substrate); the beam penetrates to a depth of a few microns, displacing some of the substrate's atoms and causing a cascade of additional collisions.

The ion implantation apparatus selected must be able to generate ions of the desired species. A gaseous source is generally used with ions being generated by boiling them off. The correct ions are separated from any others, if necessary, by bending them through a preset angle using an electromagnetic field. The selected ions are then accelerated using an electric field and strike the target substrate.

Apparatus for conducting ion beam implantation are disclosed in N. Basta, "Ion-Beam Implantation", *High Technology*, Feb. 1985; P. Sioshansi, "Ion Beam Modification of Materials for Industry", *Thin Solid Films*, 118 (1984) p. 61–71; and P. Gise et al, "Semiconductor and Integrated Circuit Fabrication Techniques", prepared by the Fairchild Management and Career Development Center, published by Reston Publishing Company, Inc., 1979, pages 80–82; all of which are incorporated by reference herein in their entirety.

Ion-beam processing is a "line-of-sight" process, the workpiece must be moved about in a steady, controlled manner during exposure for a uniform bombardment. And because implantation occurs in a vacuum, bombarded materials are not subject to convective cooling; temperatures can rise high enough to damage some materials. Obviously, the processing conditions including temperature must be such that the haptic or intraocular lens are not damaged during the process. Thus, the temperature must be suitable for the material or substrate being treated.

The basic ion beam implantation process uses energetic ion beams (approximate range 10–500 KeV) which are capable of penetrating hundreds of atomic layers into a material or substrate and change the mechanical and chemical surface properties of the material thereby improving durability and wear properties of the material.

However, ion beam implantation also generically encompasses the use of lower energy ions. Lower energy ions are used in ion beam sputtering, ion plating and plasma ion deposition. These ions are less penetrating and are generally used to build thin layer coatings on the surfaces of materials. Thus, reference to ion beam implantation for haptics is intended to cover all of the foregoing processes.

In ion beam mixing, a beam is projected onto a material or substrate during or after other deposition processes. The other processes may include ion beam sputtering, chemical vapor deposition and conventional plating. The purpose of ion beam mixing is to "stitch" the plated layer into the substrate thus preventing the plating from peeling off. In addition, in many instances where it is difficult to obtain an intense beam current of the desired ion species such as platinum, hafnium, rhodium, molybdenum, tantalum, and the like directly from the ion source, the ions are introduced by an auxiliary process into the surface. This process can take a variety of different forms from the conventional ion beam mixing to enhanced ion beam deposition. Enhanced ion beam deposition allows for a thicker deposited layer than can be obtained with either direct ion implantation or with conventional ion beam mixing.

Ion beam mixing includes combinations such as molybdenum evaporated by a sulfur beam (with the intention of forming MoS); carbon plus chromium (chromium carbide); or a variety of ion beams such as silicon, aluminum, yttrium, titanium plus boron, and the like.

In the ion beam sputtering process, an energetic ion beam is incident on the target substrate and causes sputtering of the target ions which then coat the substrate of interest. In this process, the sputtered atoms arrive at the substrate surface with enough energy to cause ionization and to deposit a coating film with good adhesion qualities. The coatings deposited in this process are under compression and manifest a dense amorphous structure. Thin films of virtually any compound can be deposited by this technique.

Plasma ion deposition involves the deposition of a hard coating. It is generally recognized that unusual phases of different coatings may be synthesized by energetic ion beams. The hard coatings produced by this method are transparent, quasi-amorphous and extremely adherent to the substrate.

In coating the haptics using the process of the present invention, a number of parameters must be considered to determine the preferred process conditions. These include the haptic material to be coated, choice of ion, ion dose and energy. These factors are balanced to obtain the optimum combination for improved resistance and cost effectiveness. The ion dose is controlled by counting the ions as they pass a detector, and the energy is controlled by changing the voltage along the acceleration chamber.

While many applications require only approximately 10,000 electron volts, other applications may use a 10-million-electron-volt (MeV) beam generator. The precise number of volts useful in the practice of the present invention is a number sufficient to adequately coat the haptic.

The dose of ions can also vary over a wide range and depend upon the area to be coated, the substrate and the desired property to be obtained. Thus, no specific dose of ions is required. Generally, the dose of ions may range from about $1 \times 10^5$ ions/cm$^2$ to about $1 \times 10^{40}$ ions/cm$^2$.

Generally, during ion beam implantation, the beam of energetic ions penetrates to a depth of about 0.05 to 2.0 μm into the haptic. The energy imparted to the ion determines the ion implantation depth. These implanted ions cause physical and chemical changes, creating new surface properties which display superior resistance to wear, friction, fatigue and corrosion.

The vacuum pressure during processing is also dependent on many of the variables defined above. The vacuum pressure generally ranges from about $1 \times 10^{-10}$ to about $1 \times 10^{-3}$ Torr.

It may also be noted that a higher ion state such as +2 or more as opposed to just +1 may be obtained, under certain conditions, thus imparting twice the energy to the ions.

The coating material preferably has biocompatibility with body tissue as well as enhanced lubricity to minimize any tendency to adhere to body tissues.

Figure 5:
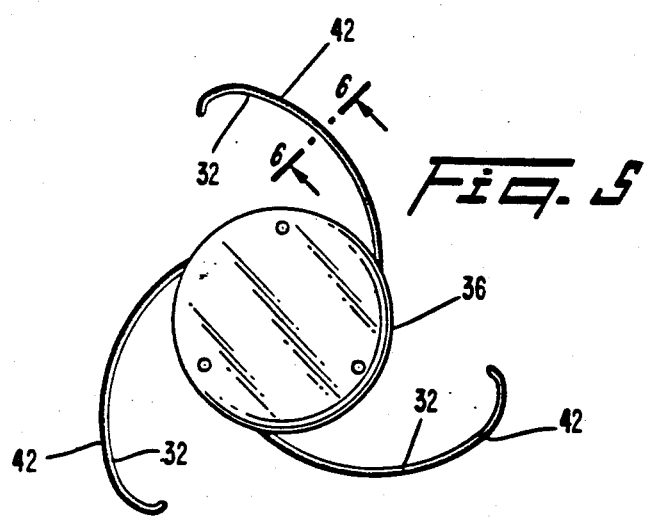
FIG. 5 is a plan view of an intraocular lens and haptic which advantageously employs another embodiment of the subject invention and shows a covering on an apical surface of the haptic strand elements.
Figure 6:
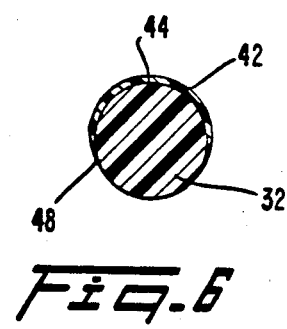
FIG. 6 is a cross-sectional view taken along section line 6—6 in FIG. 5.

An alternate embodiment of the invention is shown in FIG. 5 wherein a covering 42 extends partially around the circumference of a polypropylene core 32 of a haptic strand. A cross section of the loop is presented in FIG. 6 and discloses the cover 42 attached as a veneer onto an outer apical surface 44 of the haptic. Here the cover 42 is advantageously provided with a feathered edge 48 as it terminates at about diametrically opposite points on the apical surface 44, so as to appear as a smooth continuous surface around the circumference of the haptic element. Alternatively, a small undercut 42' may be employed on the apical surface of the haptic element to receive the coating. In this embodiment, the weight of the biocompatible protective covering material is reduced with respect to the positively buoyant polypropylene.

Figure 7:
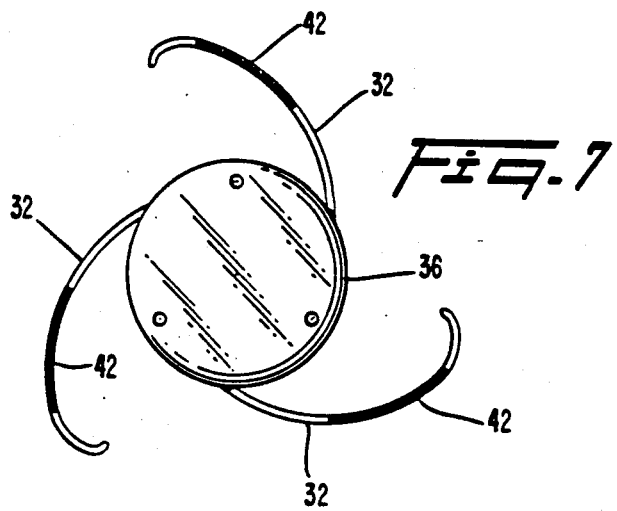
FIG. 7 is a plan view of an intraocular lens and haptic which advantageously employs another embodiment of the subject invention and shows a covering extending partially over the length of the apical surface of the haptic strand elements.
Figure 8:
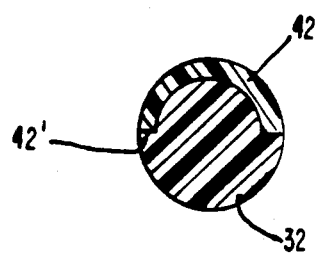
FIG. 8 is a cross-sectional view similar to FIG. 6 showing another embodiment in which a small undercut on the apical surface of the haptic strand receives the covering.

In yet another embodiment of the invention, shown in FIG. 7, the coating 42 is present only on a portion of the longitudinal dimension of the haptic strand 32. Such an arrangement provides a protective covering on those surfaces most susceptible to the deleterious conditions that are observed to be in the greatest contact with human tissue. At the same time, this embodiment is the lightest arrangement and minimizes the amount of weight added to the buoyant haptic.

The invention as presented comprehends the application of either a full circumference coating as featured in FIGS. 3 and 4 to only a portion of the haptic element as shown in FIG. 7.

In addition, the haptic core material may be any of the previously described compositions recognized in the prior art.

SUMMARY OF MAJOR ADVANTAGES OF THE INVENTION

After reading and understanding the foregoing description of the invention, in conjunction with the drawings, it will be appreciated that several advantages of the subject improved haptic element having an ion coating are obtained.

Without attempting to set forth all of the desirable features of the subject coated haptics, at least some of the major advantages of the invention include the retention of the advantageous and preferred use of polypropylene as a haptic material with the correction of the only known deficiency of the material. Here in the past it is believed by some observers that polypropylene haptic material might be subject to in-vivo alteration. Degradation, to the extent it existed, is obviated by the application of the instant biocompatible ion coating on the surface of the haptic.

Another significant advantage of the subject invention resides in provision of an advantageous haptic cover employing well known and medically accepted materials to maintain the specific gravity of less than 1.0 and flexibility of conventional strandtype haptic carrier elements. This provides increase patient acceptance by virtue of the elimination of early lens replacement due to haptic alterations and enables the patient to be fitted with an intraocular lens having a haptic which is known to be comfortable and provides a buoyant uplift to a lens body.

Further, the inventive haptic covering enables use of known haptic design and can be advantageously utilized without redesign of conventional haptic elements.

Still further, the coatings of the subject invention provide a remedy to the surface alterations observed in polypropylene haptic materials by superimposing a second layer of material having high lubricity, low friction, good flexibility and satisfactory biocompatibility.

In describing the invention, reference has been made to preferred embodiments and illustrative advantages of the invention. Those skilled in the art, however, and familiar with the instant disclosure of the subject invention, may recognize additions, deletions, modifications, substitutions and/or other changes which will fall within the purview of the subject invention and claims.

What is claimed is:

1. An intraocular lens for surgical implantation within a human eye, said intraocular lens comprising a lens body and a plurality of haptic member radiating outwardly from the lens body which are sized for operably contacting peripheral margin areas of a patient's eye to allow proper positioning, said haptic members comprising a biocompatible protective ion coating of relatively inert material placed upon the haptic element by ion beam implantation to enhance the longevity or in-vivo service life of the haptic element and to shield the haptic material from the detrimental and bioerodable effects of body fluids and tissue contact.

2. An intraocular lens as defined in claim 1, wherein said haptic members are sized for contacting peripheral margin areas of an anterior chamber or a posterior chamber of a patient's eye.

3. An intraocular lens as defined in claim 1, wherein said lens body comprises polymethylmethacrylate.

4. An intraocular lens as defined in claim 1, wherein said haptic members comprise polypropylene.

5. an intraocular lens as defined in claim 1, wherein said biocompatible protective ion coating is nitrogen, carbon, silicon, aluminum, tin, titanium, boron, nickel, chromium, zirconium, gold, germanium, xenon, platinum, phosphorus, yttrium, hafnium, rhodium, molybdenum, tantalum and combinations thereof.

6. An intraocular lens as defined in claim 5, wherein said biocompatible protective ion coating is nitrogen, carbon, silicon or aluminum.

7. An intraocular lens as defined in claim 6, wherein said biocompatible protective ion coating is nitrogen.

8. An intraocular lens as defined in claim 1, wherein said biocompatible protective ion coating coats those portions of the haptic element designed to be in contact with living tissue upon proper placement within a human eye.

9. An intraocular lens as defined in claim 1, wherein said biocompatible protective ion coating extends partially around the circumference of a polypropylene core of a haptic strand.

10. An intraocular lens as defined in claim 1, wherein said biocompatible protective ion coating is present only on a portion of the longitudinal dimension of the haptic member.

11. An intraocular lens as defined in claim 1, wherein said biocompatible protective ion coating extends around the full circumference of the haptic member and over the entire longitudinal dimension of the haptic member.

12. An intraocular lens as defined in claim 1, wherein said biocompatible protective ion coating is provided with a feathered edge as it terminates at about diametrically opposite points on the apical surface.

13. An intraocular lens as defined in claim 1, wherein said haptic element has a small undercut on the apical surface to receive the biocompatible protective ion coating.

14. An intraocular lens for surgical implantation within a human eye by placement in a posterior chamber, an anterior chamber or in an evacuated lens bag, said intraocular lens comprising a lens body and a plurality of haptic members radiating outwardly from the lens body which are sized for contacting peripheral margin areas of a posterior chamber, an anterior chamber or an evacuated lens bag to allow proper positioning of the intraocular lens within the eye, said intraocular lens comprising a lens body consisting essentially of polymethylmethacrylate, said haptic members consisting essentially of polypropylene and a biocompatible protective ion coating of relatively inert material comprising nitrogen, carbon, silicon or aluminum, placed upon the haptic element by ion beam implantation to enhance the longevity or in-vivo service life of the haptic element and to shield the haptic material from the detrimental and bioerodable effects of body fluids and tissue contact.

15. A method of making an intraocular lens for surgical implantation within a human eye, said method comprising:

providing a lens body and a plurality of haptic members radiating outwardly from the lens body operable to contact peripheral margin areas of a patient's eye to allow proper positioning of the intraocular lens within the eye and placing a biocompatible protective ion coating of relatively inert material upon the haptic members by ion implantation to enhance the longevity or in-vivo service life of the haptic element and to shield the haptic material from the detrimental and bioerodable effects of body fluids and tissue contact.

16. A method for making an intraocular lens as defined in claim 15, wherein said lens body comprises polymethylmethacrylate.

17. A method for making an intraocular lens as defined in claim 15, wherein said haptic member comprises polypropylene.

18. A method for making an intraocular lens as defined in claim 15, wherein said biocompatible protective ion coating is nitrogen, carbon, silicon, aluminum, tin, titanium, boron, nickel, chromium, zirconium, gold, germanium, xenon, platinum, phosphorus, yttrium, hafnium, rhodium, molybdenum, tantalum and combinations thereof.

19. A method for making an intraocular lens as defined in claim 18, wherein said biocompatible protective ion coating is nitrogen, carbon, silicon or aluminum.

20. A method for making an intraocular lens as defined in claim 19, wherein said biocompatible protective ion coating is nitrogen.

21. A method for correcting the vision in a patient who has had a natural lens removed comprising:

providing an intraocular lens comprising a lens body consisting essentially of polymethylmethacrylate and a plurality of haptic members radiating outwardly from the lens body which contact peripheral margin areas of a posterior chamber, an anterior chamber or an evacuated lens bag to allow proper positioning of the intraocular lens within the eye, said haptic members consisting essentially of poly-propylene, placing a biocompatible protective ion coating of relatively inert material upon the haptic members by ion implantation to enhance the longevity or in-vivo service life of the haptic members and to shield the haptic material from the detrimental and bioerodable effects of body fluids and tissue contact, and positioning the intraocular lens into a posterior chamber, an anterior chamber or an evacuated lens bag of an eye.

* * * * *